United States Patent [19]

Yanagisawa et al.

[11] 4,371,475
[45] Feb. 1, 1983

[54] 1,4-BIS-STYRYL-BENZENE DERIVATIVES AND A PROCESS FOR THE PREPARATION OF THE SAME

[75] Inventors: Takao Yanagisawa, Izumiotsu; Meguru Tanaka, Sennan, both of Japan

[73] Assignee: Showa Kagaku Kogyo Company, Ltd., Japan

[21] Appl. No.: 935,319

[22] Filed: Aug. 21, 1978

Related U.S. Application Data

[63] Continuation of Ser. No. 793,855, May 4, 1977, abandoned.

[51] Int. Cl.³ ............... C07C 143/42; D06P 1/38; C09K 11/06
[52] U.S. Cl. ................ 260/512 R; 260/512 C; 8/648; 252/301.21
[58] Field of Search ......... 260/512 C, 505 C, 512 R; 8/648; 252/301.21

[56] References Cited

U.S. PATENT DOCUMENTS 3,843,718 10/1974 Luethi ..................... 260/512 C
3,940,437 2/1976 Davidson et al. .......... 260/505 C

*Primary Examiner*—Alan Siegel
*Attorney, Agent, or Firm*—Wenderoth, Lind & Ponack

[57] ABSTRACT

This invention relates to a novel 1,4-bis-styrylbenzene derivative, in particular, suitable for use as an optical brightening agent, which is represented by the following general formula,

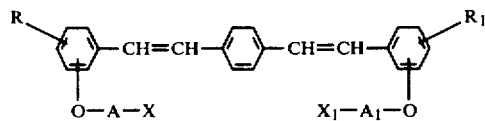

in which R and $R_1$, which may be same or different, represent a member selected from the class consisting of hydrogen atom, halogen atoms, lower alkyl groups and lower alkoxy groups, A and $A_1$, which may be same or different, represent a member of lower alkylene groups which may be substituted by a member selected from the class consisting of halogen atoms, hydroxyl group and lower alkyl groups and X and $X_1$, which may be same or different, represent a member selected from the class consisting of —COOM groups and —SO$_3$M groups wherein M represents a member selected from the class consisting of hydrogen atom, alkali metals, alkaline earth metals, organic ammoniums and guanidiniums.

12 Claims, No Drawings

1,4-BIS-STYRYL-BENZENE DERIVATIVES AND A PROCESS FOR THE PREPARATION OF THE SAME

This is a continuation, of application Ser. No. 793,855, filed May 4, 1977 now abandoned.

BACKGROUND OF THE INVENTION

1. Field of the Invention

This invention relates to new derivatives of 1,4-bis-styryl-benzene, a process for the preparation thereof and a use thereof as an optical brightening agent.

2. Description of the Prior Art

Up to the present time, some 1,4-bis-styryl-benzene derivatives have been proposed as an optical brightener. For example, Japanese Patent Publication No. 6715/1962 (corresponding to British Pat. No. 913,735) discloses those having free carboxyl group or its derivatives and/or nitrile group on the terminal benzene groups, Japanese Patent Publication No. 11678/1962 describes that a 1,4-bis-styryl-benzene derivative can be prepared by reacting benzylphosphonic acid, wherein the carbon atom bonded with phosphorus has at least one hydrogen atom and the p-position is not substituted by carboxyl group, or its ester with 1,4-dicarbonylbenzene compound, preferably, in an inert solvent in the presence of a proton acceptor, Japanese Patent Publication No. 580/1965 (corresponding to U.S. Pat. No. 3,076,020) discloses that 1,4-bis-styryl-benzene derivatives having free carboxyl groups or carbonyl oxygens on both the terminal phenyl groups are excellent as an optical brightener, Japanese Patent Publication No. 31870/1970 discloses those having methoxy groups or phenyl groups on both the terminal phenyl groups at the m-position or p-position, and Japanese Patent Application (OPI) No. 19875/1976 discloses those having sulfonic acid group on the central phenyl group.

SUMMARY OF THE INVENTION

It is an object of the present invention to provide an optical brightener which give an unobjectionable brightening effect even when used in a small amount.

It is another object of the present invention to provide a 1,4-bis-styryl-benzene derivative suitable for brightening optically organic materials such as cellulose fibers.

It is a further object of the present invention to provide a 1,4-bis-styryl benzene derivative suitable for brightening natural or synthetic nitrogen-containing fibrous materials such as silk, wool, nylon, etc.

It is a still further object of the present invention to provide an optical brightener excellent in heat resistance as well as stable at a high temperature under alkaline condition.

These objects can be attained by a 1,4-bis-styryl-benzene derivative represented by the following general formula:

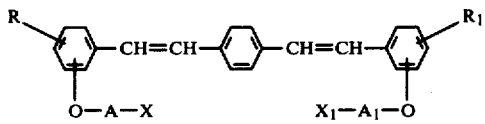

in which R and $R_1$, which may be same or different, represent hydrogen atom, halogen atoms, lower alkyl groups or lower alkoxy groups, A and $A_1$, which may be same or different, represent lower alkylene groups which may be substituted by halogen atoms, hydroxyl group or lower alkyl groups and X and $X_1$, which may be same or different, represent —COOM groups or —$SO_3M$ groups wherein M represents hydrogen atom, an alkali metal, alkaline earth metal, organic ammonium or guanidinium.

DETAILED DESCRIPTION OF THE INVENTION

We, the inventors, have made efforts to overcome the disadvantages of the prior art and consequently have found that a 1,4-bis-styryl-benzene derivative represented by the following General Formula (I),

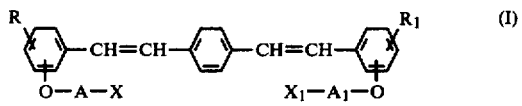

in which R and $R_1$, which may be same or different, represent hydrogen atom, halogen atoms, lower alkyl groups or lower alkoxy groups, A and $A_1$, which may be same or different, represent lower alkylene groups which may be substituted by halogen atoms, hydroxyl group, or lower alkyl groups and X and $X_1$, which may be same or different, represent —COOM groups or —$SO_3M$ groups wherein M represents hydrogen atom, an alkali metal, alkaline earth metal, organic ammonium or guanidinium, is suitable for the optical brightening of various organic materials, in particular, cellulosic fiber materials, nitrogen-containing fiber materials, synthetic resins, detergents, soaps, etc. In particular, in view of that the 1,4-bis-styryl-benzene derivative having sulfonic acid groups in both the terminal phenyl groups, disclosed in Japanese Patent Publication No. 11678/1962, has no practical brightening effect for cellulosic fibers, it is surprising that the compound of the present invention has an excellent brightening effect for materials consisting of cellulosic fibers.

In the above described General Formula (I), in general, the halogen atoms include chlorine, bromine and fluorine atoms, the lower alkyl groups include methyl, ethyl, propyl, isopropyl, butyl, isobutyl and tert-butyl groups, the lower alkoxy groups include methoxy, ethoxy, propoxy, isopropoxy, butoxy, isobutoxy and t-butoxy groups, the lower alkylene groups include methylene, ethylene, propylene and butylene groups, the alkali metals include lithium, sodium and potassium and the alkali earth metals include calcium, magnesium and barium.

The compound of the present invention, represented by General Formula (I), can readily be prepared, for example, by reacting one mol of a 1,4-xylylenephosphonic acid ester derivative represented by the following General Formula (II),

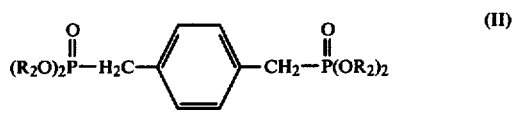

in which $R_2$ represents a lower alkyl group or phenyl group, with two mols of at least one of benzaldehyde derivatives represented by the following General Formula (III),

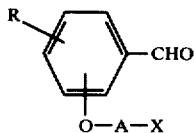

in which R, A and X have the same meanings as described above, preferably, in the presence of a proton acceptor in a hydrophilic organic solvent.

Useful examples of the hydrophilic organic solvent are formamide, dimethylformamide, diethylformamide, acetamide, dimethylacetamide and dimethyl sulfoxide, polyhydric alcohols such as ethylene glycol, ethylene glycol monomethyl ether, ethylene glycol monoethyl ether, diethylene glycol and propylene glycol, tetrahydrofuran, furfuryl alcohol and N-methylpyrrolidone.

Useful examples of the proton acceptor are alkali metal and alkaline earth metal hydroxides such as sodium hydroxide, potassium hydroxide, calcium hydroxide and barium hydroxide, alkali metal and alkaline earth metal alcoholates such as sodium methylate, potassium methylate and magnesium methylate, alkali metal and alkaline earth metal amides such as sodium amide and calcium amide, and strongly basic amines such as trialkylammonium hydroxides.

The above described reaction can be carried out at room temperature or at a temperature of at least 100° C.

The 1,4-xylylenephosphonic acid ester derivative represented by General Formula (II) is generally prepared in known manner by reacting 1,4-xylylene dichloride with an excessive amount of a phosphonic acid ester and, as the phosphonic acid ester, there are used the corresponding lower alkyl esters, preferably, methyl or ethyl ester.

The benzaldehyde derivative represented by General Formula (III), where X is sulfonic acid group, can be prepared with a high yield by reacting one mol of a hydroxybenzaldehyde derivative with one mol of a halogenated lower alkylsulfonic acid or a dehydrated cyclic compound of hydroxylated lower alkylsulfonic acid, that is, sultone compound, preferably in the presence of a basic catalyst in an inert organic solvent.

Where X is carboxylic acid group, the benzaldehyde derivative can readily be prepared by reacting one mol of a hydroxybenzaldehyde derivative with one mol of a halogenated lower fatty acid or a dehydrated cyclic compound of hydroxylated lower fatty acid, that is, lactone compound, preferably, in the presence of a caustic alkali in an aqueous medium or inert organic solvent.

Examples of the hydroxybenzaldehyde derivative which can be used in the above described reaction are as follows:

(1) salicylaldehyde
(2) 3-hydroxybenzaldehyde
(3) 4-hydroxybenzaldehyde
(4) 5-chloro-2-hydroxybenzaldehyde
(5) 2-chloro-4-hydroxybenzaldehyde
(6) 5-bromo-2-hydroxybenzaldehyde
(7) 3-bromo-4-hydroxybenzaldehyde
(8) 3-methyl-2-hydroxybenzaldehyde
(9) 4-methyl-2-hydroxybenzaldehyde
(10) 5-methyl-2-hydroxybenzaldehyde
(11) 2-methyl-4-hydroxybenzaldehyde
(12) 5-tert-butyl-2-hydroxybenzaldehyde
(13) 4-methoxy-2-hydroxybenzaldehyde
(14) 5-methoxy-2-hydroxybenzaldehyde
(15) 2-methoxy-4-hydroxybenzaldehyde
(16) 3-ethoxy-4-hydroxybenzaldehyde
(17) 3-isopropoxy-4-hydroxybenzaldehyde
(18) 4-methoxy-3-hydroxybenzaldehyde These hydroxybenzaldehyde derivatives and the benzaldehyde derivatives represented by the foregoing General Formula (III) can be used in the form of the corresponding acetal.

Useful examples of the halogenated lower alkylsulfonic acid or the dehydrated cyclic compound of hydroxylated lower alkylsulfonic acid are as follows:

(1) 1,2-ethanesultone
(2) 1,3-propanesultone
(3) 1,3-butanesultone
(4) 1,4-butanesultone
(5) 1,3-octanesultone
(6) 1-chloroethanesulfonic acid
(7) 2-chloroethanesulfonic acid
(8) 2-chloro-1-hydroxyethanesulfonic acid
(9) 3-chloro-2-hydroxypropanesulfonic acid Useful examples of the halogenated lower fatty acid or the dehydrated cyclic compound of hydroxylated lower fatty acid are as follows:

(1) monochloroacetic acid
(2) dichloroacetic acid
(3) α-methylmonochloroacetic acid
(4) β-chloropropionic acid
(5) α,α-dichloropropionic acid
(6) α-, β- or γ-chlorobutanic acid
(7) propiolactone
(8) γ-butyrolactone
(9) α-methylpropiolactone
(10) γ-methylbutyrolactone
(11) γ-isopropylbutyrolactone
(12) δ-valerolactone The 1,4-bis-styryl-benzene derivative of the present invention is available for optically brightening various organic materials. For example, cellulosic fibers, in particular, cotton can be optically brightened to an excellent whiteness. As a dyeing process, there are the ordinary dip dyeing process and, in addition, the high temperature continuous brightening process such as pad steaming process, pad baking process, etc. Furthermore, the known dyeing process available for cellulose fibers can also be used, for example, the so-called solvent dyeing process using organic solvents.

Using the compound of the present invention, for example, represented by the following formula,

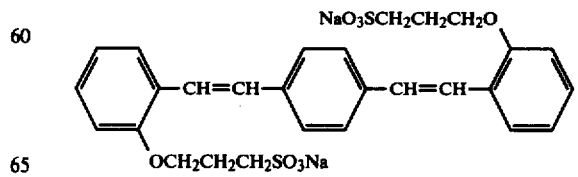

as prepared in Example 1, and the known compound, for example, represented by the following formula,

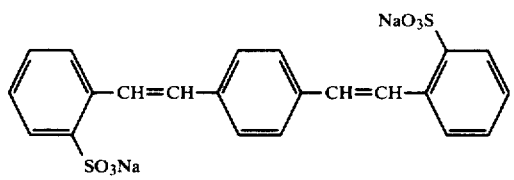

as described in the foregoing Japanese Patent Publication No. 11678/1962, dyeing baths are prepared with controlling from the optical density to a same concentration (0.2% by weight aqueous solution) and cotton fabrics are padded therein. As to the thus resulting brightened fabrics, the fluorescent reflectance at 435 mμ was measured to obtain results as shown in Table 1 when the reflectance of the standard white plate of magnesium oxide is regarded as "100%".

TABLE 1

|  | 0.2% Padding |
|---|---|
| Compound of Present Invention | 119.9% |
| Known Compound | 110.4% |

The compounds of the present invention are capable of optically brightening natural or synthetic nitrogen-containing fibrous materials, for example, silk, wool and nylon in an excellent whiteness. The compounds of the present invention are very excellent in heat resistance and thus particularly suitable for the high temperature continuous dyeing of synthetic polyamide fibrous materials. The high temperature continuous dyeing set forth herein is carried out by padding a synthetic polyamide fiber material with a dilute aqueous solution of a brightener, previously drying and then subjecting to soaping at a high temperature, e.g., 150° to 200° C. in a certain period of time, i.e., 1 to 3 minutes.

Using a 4,4'-bis-triazolylstilbene-2,2'-disulfonic acid derivative, well known in the art, (Blankophor CL, manufactured by Bayer A.G.) and the compound of the present invention, as prepared in Example 1, with a same concentration and under a same condition, nylon fabrics are brightened and then subjected to measurement of the fluorescent reflectance at 440 mμ for comparison, thus obtaining results as shown in Table 2, when the reflectance of the standard non-treated fabric is regarded as "100%":

TABLE 2

|  | Reflectance (440 mμ) |
|---|---|
| Known Compound | 121.4% |
| Compound of Present Invention | 125.8% |

In addition, the compound of the present invention has also an excellent brightening effect for wool. When wool fabrics are optically brightened in conventional manner using Tinopal WG pyrazoline type compound, manufactured by Ciba Geigy Co.) and Uvitex NFW (bis-stilbene type compound, manufactured by Ciba Geigy Co.), well known as a brightener for wool, for example, the former brightener gives a considerably greenish brightening effect and the latter brightener reversely gives a somewhat reddish brightening effect. On the other hand, when using the compound of the present invention, there is obtained a brightening effect of very clear neutral whiteness and the visual whiteness given thereby is much better than that of the above described two known brighteners. The fluorescent reflectances of these brightened fabrics, at 440 mμ, are tabulated below based on that of the non-treated fabric:

|  | 0.5% (owf) | 1.0% (owf) |
|---|---|---|
| Tinopal WG | 118.4% | 124.1% |
| Uvitex NFW | 113.9% | 119.1% |
| Compound of Present Invention | 121.3% | 131.4% |

Furthermore, the compound of the present invention is capable of optically brightening bases such as soaps, detergents, fats and oils and waxes in an excellent whiteness. In particular, the compound of the invention not only optically brightens detergent bases for industrial use or home use in washing fibrous articles to thus increase their commercial value, but also makes clear the whiteness of fibrous articles treated with a detergent containing the compound of the present invention. Therefore, the compound of the invention is also suitable for use as an additive to detergents.

A compound represented by the following formula,

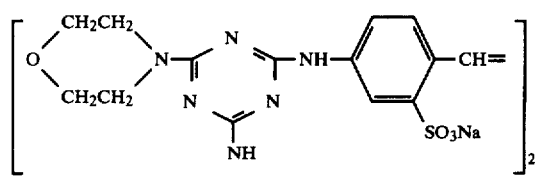

known as a brightener for detergents in the art, and the compound of the present invention, as prepared in Examples 17 and 18, are respectively added to 10 g of a powdered detergent having the following composition:

|  | parts by weight |
|---|---|
| LAS (Linear Alkylbenzene Sulfonate) | 16 |
| ABS (Alkylbenzene Sulfonate) | 4 |
| Sodium Tripolyphosphate | 30 |
| Sodium Silicate No. 2 | 2 |
| Sodium Toluenesulfonate | 5 |
| CMC (Carboxy Methyl Cellulose) | 1 |
| Sodium Sulfate | 42 | in a proportion of 0.2% and 0.5% based on the weight of the detergent, mixed with a small amount of water to form slurry, subjected to evaporation to dryness in an evaporating dish on a water bath and ground to obtain brightened detergent powders. The so obtained detergent powders are then subjected to measurement of the fluorescent reflectance at 440 mμ, thus obtaining results as shown in Table 3 when the reflectance of the non-treated detergent powder is regarded as "100%":

TABLE 3

|  | Reflectance (44 mμ) | |
|---|---|---|
|  | 0.2% | 0.5% |
| Known Compound | 101.5% | 107.0% |
| Compound of Example 17 | 118.2% | 120.9% |
| Compound of Example 8 | 111.9% | 118.3% |

As is evident from this result, the compound of the present invention is stable even at a high temperature under alkaline condition, in addition to the excellent heat resistance as described hereinbefore, Therefore, the compound of the present invention is sufficiently resistant to even a processing of blending with an alkaline detergent as described above and subjecting to drying at a high temperature, for example, spray drying and does not discolor the detergent base into yellow.

The compound of the present invention can also be used for optically brightening pulps or papers. To this end, any of the known processes can be applied, for example, by adding into pulp, surface coating, size pressing, etc. Above all, the paper surface coating process is most important. That is to say, in this case, the compound of the invention is used by adding to starch, casein, white pigments or synthetically obtainable surface caoting agents before or after coating papers therewith.

Furthermore, the compound of the present invention can be used for various photographic purposes, for example, for electrophotographic copying, for supersensitization, for optically brightening photographic layers or photographic printing papers, or as a scintillator together with white pigments such as titanium oxide.

The compound of the present invention is also useful for brightening optically various synthetic or semi-synthetic organic high molecular materials, for example, polyamides, polyurethanes, polyvinyl alcohol, polycarbonates, epoxide resins, amino resins such as urea resins, melamine resins, benzoguanamine resins, urea-melamine resins or mixtures thereof, and other materials such as cellulose esters and cellulose ethers. Application of the compound of the present invention can be carried out at any step of processings, for example, before or during forming these resin materials. Therefore, the compound of the invention can be added to compositions for forming or molding, for example, in the case of preparing films or other formed articles. The compound of the invention can also be dissolved, dispersed or finely divided in spinning compositions before spinning. Moreover, the compound of the present invention can be added to starting materials, reaction mixtures or intermediates used for the production of the above described synthetic or semi-synthetic organic materials, i.e., before or during chemical reactions such as polycondensation, polymerization and polyaddition.

When using the compound of the present invention, the concentration thereof in a material to be treated can be varied within a wide range. Even if the compound of the invention is used in a very thin concentration, e.g., 0.001% by weight, an excellent brightening effect can be achieved, and the most useful concentration ranges from 0.01 to 1% by weight or to at most 2% by weight.

The compound of the present invention can generally be used together with the commonly used dyeing aids, such for example as sodium sulfate, sodium chloride, urea, acetic acid and surfactants and, of course, can also be used with suitable dyes, pigments or other optical brightening agents. Since the compound of the present invention is stable for reducing agents such as hydrosulfites or for chemical bleaching agents, in particular, chlorine-containing bleaching agents, the use as a brightener for various fibrous materials is more enlarged. As occasion demands, the compounds of the invention can be used with various additives for resins, for example, antioxidants, antistatic agents, ultraviolet absorbers, heat stabilizers and fillers.

A brightening agent containing the compound of the present invention as an effective constituent can be in any form of powders, granules, pastes, dispersions, emulsions or thickened liquors. In the case of a powdered form or granular form, the alkaline earth metal salt or organic amine salt of General Formula (I) can be used but, in many cases, the alkali metal salt is preferably used. In the case of a paste or dispersion, the less soluble salt of General Formula (I), in particular, less soluble alkylamine salt or guanidine salt is mechanically pulverized and dispersed. In the case of a thickened liquor, the alkali metal salt of General Formula (I) may be dissolved by a suitable known dissolution accelerator, but, preferably, the more soluble organic amine salt of General Formula (I), in particular, alkanolamine salt is used. Anyway, it is a precondition for obtaining a stable concentrated liquid product to remove inorganic salts present as far as possible.

The less soluble or more soluble organic amine salt according to the present invention can readily be obtained by neutralizing the corresponding free acid with the desired organic amine. At this time, the organic amine can of course be used in an excessive quantity.

The present invention will be further illustrated in greater detail by the following examples. It will be self-evident to those skilled in the art that the ratios, ingredients in the following formulations and the order of operations can be modified within the scope of the present invention. Therefore, the present invention is not to be interpreted as being limited to the following examples.

EXAMPLE 1

(A) Preparation of a compound represented by the following formula:

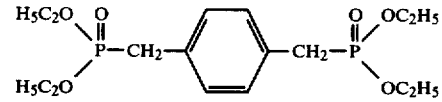

50 g of triethyl phosphite ($P(OC_2H_5)_3$) was added to 17.5 g of 1,4-xylylene dichloride and stirred with refluxing for 9 hours. The excessive triethyl phosphite was distilled off under reduced pressure and the residue was diluted with ligroin, followed by standing to cool, thus precipitating a crystal. The resulting crystal was filtered, washed with a small amount of ligroin and then dried to obtain a white crystal of phosphonic acid ester derivative corresponding to the above described formula, melting at 71° to 73.5° C.

(B) Preparation of a compound represented by the following formula:

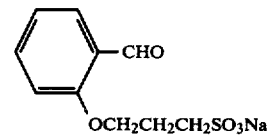

61 g of salicylaldehyde was dissolved in 400 ml of ethanol, to which a solution of 20 g of caustic soda in a small amount of water was added, to precipitate sodium salt of salicylaldehyde. With heating the whole, refluxing and stirring, 63 g of propanesultone was dropwise added thereto for a period of time of about 20 minutes, stirred for another 2 hours and then a small amount of water was added to the reaction mixture to dissolve completely the precipitate. After cooling, the precipitated crystal was separated by filtration, washed adequately with ethanol and dried to obtain a benzaldehyde derivative represented by the above described formula.

(C) Preparation of a compound represented by the following formula:

7.6 g of the phosphonic acid ester derivative obtained in (A) and 12.8 g of the aldehyde derivative obtained in (B) were dissolved in 100 ml of N,N-dimethylformamide, to which 10 g of powdered caustic potassium below 20° C. was added. At this time, the temperature rised somewhat. The mixture was stirred at 20° to 25° C. for 2 hours and then reacted at 40° C. for 30 minutes. The reaction mixture was mixed with 300 ml of water, heated to some extent to dissolve the content and a small amount of insoluble substance was removed by filtration. To this filtrate was added hydrochloric acid to a weak alkalinity and then 40 g of sodium chloride was added thereto to salt out a crystal. The thus precipitated flaky crystal was separated by filtration, washed with a small amount of water and dried. The 1,4-bis-styrylbenzene derivative represented by the above described formula, thus obtained, was recrystallized from water and subjected to elementary analysis, thus obtaining results tabulated below:

|  | C | H | O | S |
|---|---|---|---|---|
| Calculated | 55.81 | 4.68 | 21.24 | 10.64 |
| Found | 55.54 | 4.48 | 21.14 | 10.52 |

EXAMPLE 2

The procedure of Example 1-(B) was repeated except that instead of the salicylaldehyde, the same amount of 3-hydroxybenzaldehyde was reacted and there was thus obtained a benzaldehyde derivative represented by the following formula:

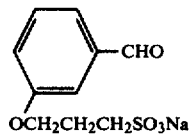

When 12.8 g of this benzaldehyde derivative was reacted with 7.6 g of the phosphonic acid ester derivative obtained in Example 1-(A) according to the procedure of Example 1-(C), there was formed a 1,4-bis-styrylbenzene derivative represented by the following formula:

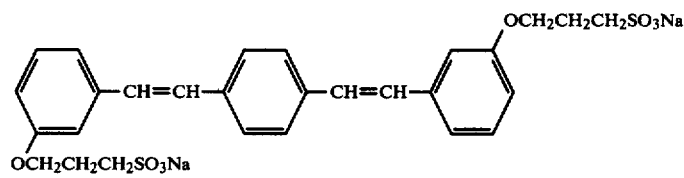

The resulting crystal was recrystallized from water and then subjected to elementary analysis, thus obtaining results tabulated below:

|  | C | H | O | S |
|---|---|---|---|---|
| Calculated | 55.81 | 4.68 | 21.24 | 10.64 |
| Found | 55.42 | 4.75 | 20.85 | 10.48 |

EXAMPLE 3

The procedure of Example 1-(B) was repeated except that instead of the salicylaldehyde, 68 g of 2-methyl-4-hydroxybenzaldehyde was reacted and there was thus obtained a benzaldehyde derivative represented by the following formula:

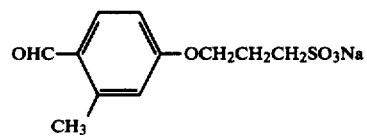

When 13.6 g of this benzaldehyde derivative was reacted with 7.6 g of the phosphonic acid ester derivative obtained in Example 1-(A) according to the procedure of Example 1-(C), there was formed a 1,4-bis-styrylbenzene derivative represented by the following formula,

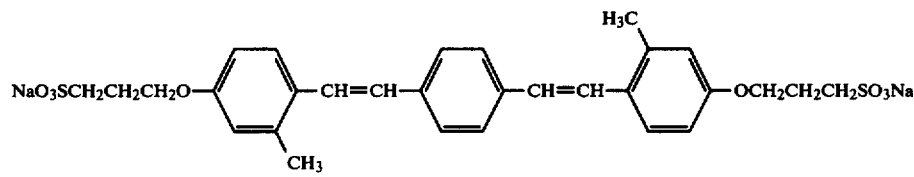

The resulting crystal was recrystallized from water and then subjected to elementary analysis to obtain the following results:

|  | C | H | O | S |
|---|---|---|---|---|
| Calculated | 57.13 | 5.11 | 20.29 | 10.17 |
| Found | 56.82 | 4.92 | 20.54 | 9.85 |

EXAMPLE 4

The procedure of Example 1-(B) was repeated except that 77 g of 3-methoxy-4-hydroxybenzaldehyde was used in place of the salicylaldehyde and 72 g of 1,4-butanesultone was used in place of the propanesultone and there was obtained a benzaldehyde derivative represented by the following formula:

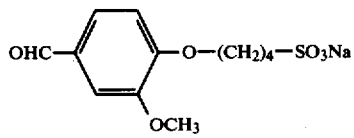

When 14.9 g of this benzaldehyde derivative was reacted with 7.6 g of the phosphonic acid ester derivative obtained in Example 1-(A) according to the procedure of Example 1-(C), there was formed a 1,4-bis-styrylbenzene derivative represented by the following formula:

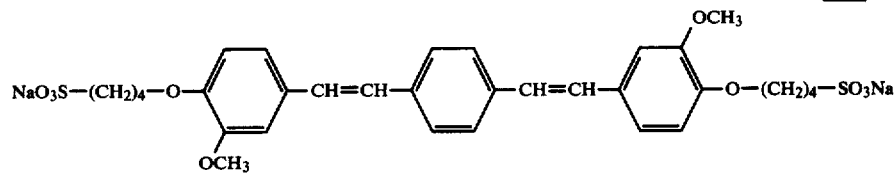

The product was recrystallized from water and then subjected to elementary analysis, thus obtaining results tabulated below:

|  | C | H | O | S |
|---|---|---|---|---|
| Calculated | 55.64 | 5.25 | 23.16 | 9.28 |
| Found | 55.17 | 5.42 | 23.45 | 9.56 |

EXAMPLE 5

6.4 g of the benzaldehyde derivative obtained in Example 1-(B), 6.4 g of the benzaldehyde derivative obtained in Example 2 and 7.6 g of the phosphonic acid ester derivative obtained in Example 1-(A) were reacted according to the procedure of Example 1-(C) and there was thus obtained a mixture of compounds represented by the following formulas:

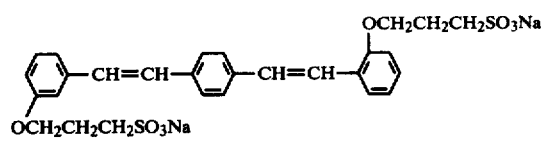

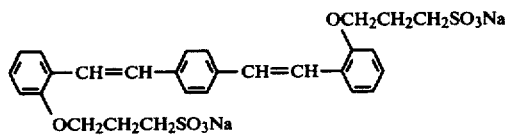

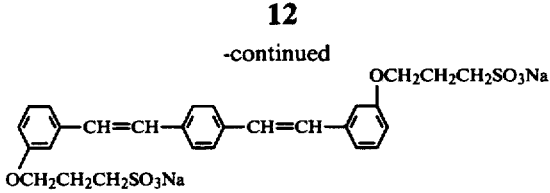

Such a mixture can similarly be used as an optical brightening agent.

EXAMPLE 6

6.1 g of salicylaldehyde and 20 g of caustic soda were dissolved in 300 ml of water and heated at approximately 70° C. with agitation, to which a slightly alkaline solution of 96.2 g of 1-chloroethanesulfonic acid and 24 g of caustic soda in 250 ml of water was dropwise added for about 30 minutes. The mixture was then heated to 95° to 100° C., reacted for about 3 hours and allowed to stand, after which the reaction mixture was made strongly acidic by concentrated hydrochloric acid. The precipitated crystal was separated by filtration, washed with water and dried to obtain a benzaldehyde derivative represented by the following formula:

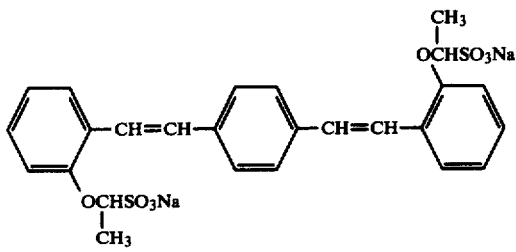

when 11.1 g of this benzaldehyde derivative was reacted with 7.6 g of the phosphonic acid ester derivative obtained in Example 1-(A) according to the procedure of Example 1-(C), there was formed a 1,4-bis-styrylbenzene derivative represented by the following formula:

The product was recrystallized from water and then subjected to elementary analysis to obtain results tabulated below:

|  | C | H | O | S |
|---|---|---|---|---|
| Calculated | 59.28 | 4.55 | 24.10 | 12.07 |
| Found | 59.84 | 4.27 | 23.87 | 12.54 |

When a benzaldehyde derivative obtained by the use of 81 g of 2-chloro-1-hydroxyethanesulfonic acid in place of the 1-chloro-ethanesulfonic acid in this example was reacted with the phosphonic acid ester derivative in an analogous manner, there was obtained a mixture of 1,4-bis-styryl-benzene derivatives represented by the following formulas:

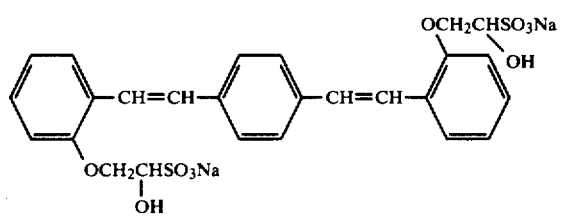

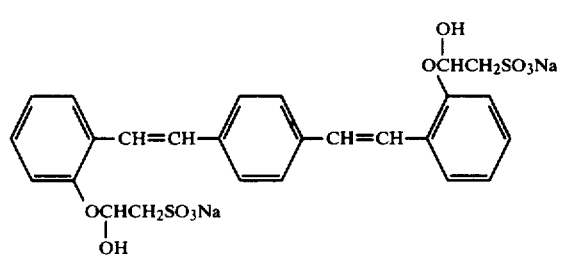

EXAMPLE 7

The procedure of Example 1-(B) was repeated except that instead of the salicylaldehyde, 78 g of 5-chlorosalicylaldehyde was used and similarly reacted and there was obtained a benzaldehyde derivative represented by the following formula:

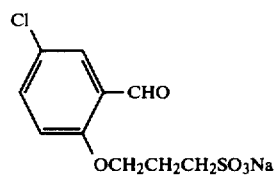

When 7.2 g of this benzaldehyde derivative and 6.4 g of the benzaldehyde derivative obtained in Example 1-(B) were reacted with 7.6 g of the phosphonic acid ester derivative obtained in Example 1-(A) according to the procedure of Example 1-(C), there was formed a mixture of compounds represented by the following formulas:

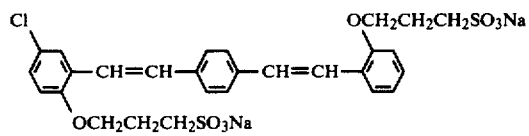

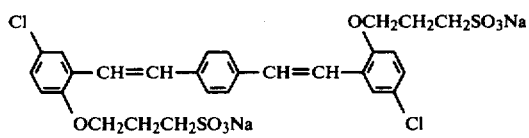

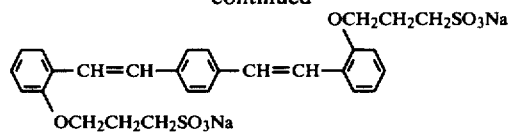

EXAMPLE 8

(A) 61 g of salicylaldehyde and 20 g of caustic soda were dissolved in 300 ml of water and heated at approximately 70° C. with agitation, to which a slightly alkaline solution of 47.3 g of monochloroacetic acid and 20 g of caustic soda dissolved in 200 ml of water was dropwise added for about 30 minutes. The mixture was then heated to 95° to 100° C., reacted for about 3 hours and allowed to stand, after which the reaction mixture was made strongly acidic by concentrated hydrochloric acid. The precipitate crystal was separated by filtration, washed with water and dried to obtain a benzaldehyde derivative represented by the following formula:

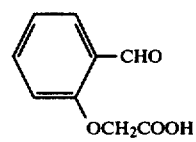

(B) When 8.6 g of the so obtained benzaldehyde derivative and 7.6 g of the phosphonic acid ester derivative obtained in Example 1-(A) were reacted according to the procedure of Example 1-(C), there was obtained a 1,4-bis-styryl-benzene derivative represented by the following formula:

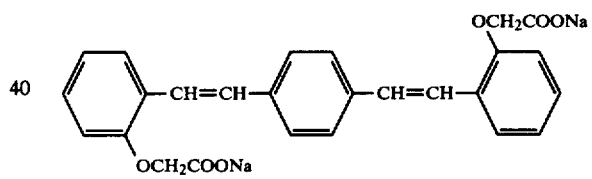

The product was recrystallized from water and then subjected to elementary analysis to obtain results tabulated below:

|  | C | H | O |
|---|---|---|---|
| Calculated | 66.01 | 4.23 | 20.13 |
| Found | 65.62 | 4.15 | 20.52 |

EXAMPLE 9

The procedure of Example 8-(A) was repeated except that 61 g of 2-chloropropionic acid was used instead of the monochloroacetic acid and reacted and there was thus obtained a benzaldehyde derivative represented by the following formula:

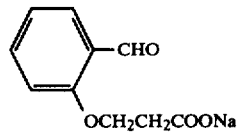

When 9.4 g of this benzaldehyde derivative was reacted with 7.6 g of the phosphonic acid ester derivative obtained in Example 1-(A) according to the procedure of Example 1-(C), there was formed a 1,4-bis-styryl-benzene derivative represented by the following formula:

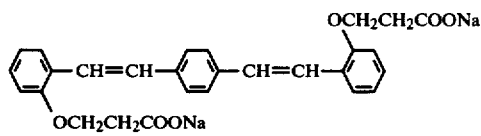

The so obtained product was purified by recrystallization from water and then subjected to elementary analysis to obtain results tabulated below:

|  | C | H | O |
|---|---|---|---|
| Calculated | 66.93 | 4.82 | 19.11 |
| Found | 67.21 | 4.55 | 18.76 |

EXAMPLE 10

The procedure of Example 8-(A) was repeated except that 61 g of 1-chloropropionic acid was used instead of the monochloroacetic acid and similarly reacted and there was thus obtained a benzaldehyde derivative represented by the following formula:

9.4 g of the resulting benzaldehyde derivative was reacted with 7.6 g of the phosphonic acid ester derivative obtained in Example 1-(A) according to the procedure of Example 1-(C) to obtain a 1,4-bis-styryl-benzene derivative represented by the following formula:

[structure: 1,4-bis-styryl-benzene with OCHCOONa/CH3 substituents on both terminal phenyl rings]

The resulting product was purified by recrystallization from water and then subjected to elementary analysis to obtain results tabulated below:

|  | C | H | O |
|---|---|---|---|
| Calculated | 66.93 | 4.82 | 19.11 |
| Found | 66.43 | 4.62 | 18.65 |

4.3 g of the benzaldehyde derivative obtained in Example 8-(A) and 4.7 g of the benzaldehyde derivative obtained in Example 9 were reacted with 7.6 g of the phosphonic acid ester derivative obtained in Example 1-(A) according to the procedure of Example 1-(C) and there was thus obtained a mixture of compounds represented by the following formulas:

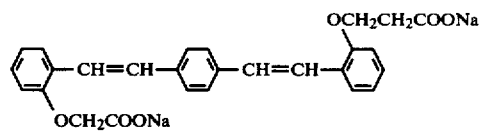

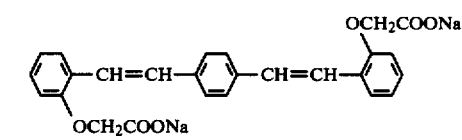

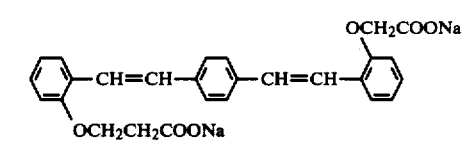

1,4-bis-styryl-benzene derivatives shown in the following table were prepared in an analogous manner. In this table, $R = R_1$ and $-O-A-X = -O-A_1-X_1$ unless otherwise indicated and the numeral indicating the position of each substituent is based on the group $-CH=CH-$. The results of elementary analysis are shown with calculated values (upper: "Calculated"; lower: "Found" in each example).

TABLE 4

| | | | Elementary Analysis | | | |
|---|---|---|---|---|---|---|
| Example | R,R$_1$ | —O—A—X, —O—A$_1$—X$_1$ | C | H | O | S |
| 12 | H | 2-OCH$_2$CH$_2$SO$_3$Na | 54.16 | 4.20 | 22.20 | 11.12 |
| | | | 54.52 | 4.42 | 21.78 | 10.82 |
| 13 | 4-CH$_3$ | 2-OCH$_2$CH$_2$SO$_3$Na | 55.81 | 4.68 | 21.24 | 10.64 |
| | | | 55.49 | 4.51 | 21.06 | 11.12 |
| 14 | 5-Cl | 2-OCHCH$_2$CH$_2$SO$_3$Na<br>    \|<br>    CH$_3$ | 51.66<br>52.21 | 4.05<br>4.10 | 18.35<br>18.11 | 9.19<br>8.86 |
| 15 | 2-Cl | 4-OCHCH$_2$CH$_2$SO$_3$Na<br>    \|<br>    (CH$_2$)$_4$.CH$_3$ | 55.17<br>54.78 | 5.40<br>5.35 | 16.33<br>15.92 | 8.18<br>7.97 |

TABLE 4-continued

| Example | R,R$_1$ | —O—A—X, —O—A$_1$—X$_1$ | C | H | O | S |
|---|---|---|---|---|---|---|
| 16 | 3-Br | 4-OCH$_2$CH$_2$CH$_2$SO$_3$Na | 44.23 | 3.45 | 16.83 | 8.43 |
|   |   |   | 43.85 | 3.23 | 16.57 | 8.21 |
| 17 | 5-CH$_3$ | 2-OCH$_2$CH$_2$CH$_2$SO$_3$Na | 57.13 | 5.11 | 20.29 | 10.17 |
|   |   |   | 56.78 | 4.92 | 19.88 | 9.84 |
| 18 | 5-C(CH$_3$)$_3$ | 2-OCH$_2$CH$_2$CH$_2$SO$_3$Na | 60.49 | 6.20 | 17.91 | 8.97 |
|   |   |   | 60.15 | 6.08 | 18.02 | 9.15 |
| 19 | CH$_3$<br>\|<br>3-OCH<br>\|<br>CH$_3$ | 4-OCH$_2$CH$_2$CH$_2$SO$_3$Na | 56.81 | 5.61 | 22.26 | 8.92 |
|   |   |   | 57.03 | 5.41 | 21.95 | 8.64 |
| 20 | 4-OCH$_3$ | 2-OCH$_2$CH$_2$CH$_2$SO$_3$Na | 54.37 | 4.87 | 24.14 | 9.68 |
|   |   |   | 54.12 | 4.62 | 24.44 | 9.45 |
| 21 | 2-Cl | 4-OCH$_2$COONa | 57.48 | 3.34 | 17.67 |   |
|   |   |   | 57.18 | 3.22 | 17.93 |   |
| 22 | H | 2-OCHCOONa | 57.48 | 3.34 | 17.67 |   |
|   |   |   | 57.16 | 3.18 | 17.95 |   |
| 23 | 4-CH$_3$ | Cl<br>\|<br>2-OCH$_2$COONa | 66.93 | 4.81 | 19.11 |   |
|   |   |   | 67.21 | 4.89 | 19.41 |   |
| 24 | H | 2-OCH$_2$CH$_2$CH$_2$COONa | 67.92 | 5.32 | 18.09 |   |
|   |   |   | 68.22 | 5.35 | 17.87 |   |
| 25 | H | 2-OCHCH$_2$CH$_2$COONa<br>\|<br>CH$_3$ | 68.81 | 5.77 | 17.19 |   |
|   |   |   | 68.45 | 5.58 | 17.32 |   |

Some applied examples of the compound of the present invention will be given below:

1-(A)

Padding process of cotton fabric (broad)

An optical brightening agent was dissolved in water in a concentration of 0.2 to 0.4% by weight to prepare a dyeing bath, in which the fabric was subjected to 1 dip and 1 nip while adjusting the pick-up to 70%. After drying at 60° to 65° C. for 30 minutes, there was obtained a cotton fabric optically brightened in a clear whiteness.

1-(B) Dip dyeing process of cotton fabric (knit)

Optical Brightener: 0.1–0.5% (owf)
Anhydrous Sodium Sulfate: 10% (owf)
Bath Ratio: 1:20 (owf)

The fabric was dipped in a dyeing bath having the above described formulation, treated at 25° C. for 20 minutes, squeezed and dried at 60° to 65° C.

2. High temperature dyeing process of nylon (plain wearing fabric)

An optical brightening agent was dissolved in water in a concentration of 5 g/liter to prepare a dyeing bath, in which the fabric was subjected to 1 dip and 1 nip while adjusting the pick-up to 70%. The fabric was previously dried at 80° to 100° C. for about 3 minutes, and subjected to hot air treatment at 180° to 190° C. for 1 to 0.5 minute, soaping at 70° C. for 30 minutes in a soaping bath having the following formulation,

| Monogen (Commercial Name, made by Daiichi Kogyo Seiyaku Co.) | 2 g/liter |
|---|---|
| Soda Ash | 2 g/liter |
| Bath Ratio | 1 : 50 (owf) | washing with water and drying.

3. Dip dyeing process of wool (muslin) using hydrosulfite

An optical Brightener: 0.5–1.0% (owf)
Acetic Acid: 2% (owf)
Hydrosulfite: 0.5% (owf)
Bath Ratio: 1:50 (owf)

The material was dipped in a dyeing bath having the above described formulation at 60° C. for 30 minutes, washed with water and dried.

4. Brightening process of amino resins 100 g of urea, 200 g of formalin (37%, neutral) and 5 g of hexamethylenetetramine were heated and reacted to obtain a resinous liquor, to which 60 g of α-cellulose, 0.05 g of ammonium chloride, 0.2 g of zinc stearate and 0.5 g of zinc white were added, and the resulting mixture was adequately kneaded. The mixture was dried at 80° C. for 90 minutes in an air drier and ground by means of a pot mill. To the so obtained fine powder was added the optical brightener of the present invention, preferably, less soluble organic amine salt of General Formula (I), in particular, triethylamine salt or guanidine salt in a proportion of 0.1% by weight on the whole composition. When this composition was molded in known manner, there was obtained an urea resin molding optically brightened in a very clear whiteness.

The compound of the present invention, less soluble organic amine salt, used in the above described applied example, was prepared as follows.

For example, the compound (sodium salt) obtained in Example 1-(C) was dissolved in water with heating and the resulting solution was made strongly acidic by addition of an excessive quantity of concentrated hydrochloric acid, followed by allowing to stand and cool. The formed precipitate was separated by filtration and washed with water to remove the excessive hydrochloric acid. The filter cake was again dispersed in water, mixed with a somewhat excessive amount of triethylamine to make alkaline and heated at 70° to 80° C. with agitation. After cooling, the resulting precipitate was separated by filtration, washed with water, dried and ground to obtain a white powder of the corresponding triethylamine salt.

5. Surface coating process of paper for printing 166 g of casein, 48 g of concentrated ammonia water and 300 g of water were heated, dissolved and further diluted with water to 1000 g.

Clay: 80 g
Calcium Carbonate: 20 g
Styrene-Butadiene Copolymer Latex: 15 g
Casein Solution Prepared As Above: 66 g The above described composition was adequately mixed and diluted with water to 250 g, to which 0.2 g of the compound of the present invention (Example 12) was added to prepare a coating composition. The composition was coated onto a sized printing paper, followed by drying, to thus give an optically brightened printing paper with a clear whiteness.

6. Brightening process of photographic printing paper (Process of coating baryta paper)

90 g of a 5% aqueous solution of gelatin, 2 g of a 3.7% aqueous solution of formalin and 1 g of a 0.5% nonionic active agent were mixed, in which 0.03 g of the compound of the present invention (Example 13) was dissolved, and the resulting coating composition was applied to a baryta paper, followed by drying, thus obtaining an optically brightened baryta paper with a very clear whiteness.

What is claimed is:

1. A 1,4-bis-styryl-benzene derivative of the formula

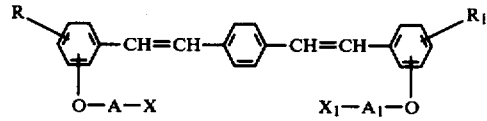

in which R and $R_1$, which may be same or different, each represent hydrogen atom, halogen atoms, lower alkyl groups or lower alkoxy groups, A and $A_1$, which may be same or different, each represent lower alkylene groups which may be substituted by halogen atoms, hydroxyl group or lower alkyl groups and X and $X_1$, which may be same or different, each represent the —$SO_3M$ groups wherein M represents hydrogen atom, an alkali metal, alkaline earth metal, organic ammonium or guanidinium.

2. The 1,4-bis-styryl-benzene derivative as defined in claim 1, wherein R and $R_1$, being same, represent hydrogen atom, chlorine atom, bromine atom, methyl group, tert-butyl group, methoxy group or isopropoxy group, A and $A_1$, being same, represent methylene, methylmethylene, chloromethylene, ethylene, hydroxyethylene, propylene, methylpropylene, pentylpropylene or butylene group, and X and $X_1$, being same, represent the —$SO_3Na$ group.

3. The 1,4-bis-styryl-benzene derivative as defined in claim 2, wherein R and $R_1$ represent hydrogen atom, A and $A_1$, being same, represent methylene, methylmethylene, chloromethylene, ethylene, hydroxyethylene, propylene or methylpropylene group and X and $X_1$, being same, represent the —$SO_3Na$ group.

4. The 1,4-bis-styryl-benzene derivative as defined in claim 2, wherein R and $R_1$ represent methyl group, A and $A_1$, being same, represent methylene, ethylene or propylene group and X and $X_1$, being same, represent the —$SO_3Na$ group.

5. The 1,4-bis-styryl-benzene derivative as defined in claim 2, wherein R and $R_1$ represent chlorine atom, A and $A_1$, being same, represent methylene, methylpropylene or pentylpropylene group and X and $X_1$, being same, represent the —$SO_3Na$ group.

6. The 1,4-bis-styryl-benzene derivative as defined in claim 2, wherein R and $R_1$ represent bromine atom, A and $A_1$, represent propylene group and X and $X_1$ represent —$SO_3Na$ group.

7. The 1,4-bis-styryl-benzene derivative as defined in claim 2, wherein R and $R_1$ represent methoxy group, A and $A_1$, being same, represent propylene or butylene group and X and $X_1$ represent —$SO_3Na$ group.

8. The 1,4-bis-styryl-benzene derivative as defined in claim 2, wherein R and $R_1$ represent tert-butyl group, A and $A_1$ represent propylene group and X and $X_1$ represent —$SO_3Na$ group.

9. The 1,4-bis-styryl-benzene derivative as defined in claim 2, wherein R and $R_1$ represent isopropoxy group, A and $A_1$ represent propylene group and X and $X_1$ represent —$SO_3Na$ group.

10. The 1,4-bis-styryl derivative of claim 1 which is

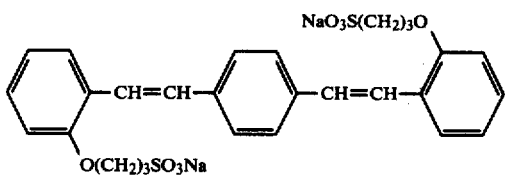

11. An optical brightener containing the 1,4-bis-styryl-benzene derivative as defined in claim 1 as an effective constituent.

12. A method for optically brightening organic materials with the 1,4-bis-styryl-benzene derivative as defined in claim 1.

* * * * *